(12) United States Patent
Vanden Hoek et al.

(10) Patent No.: US 6,673,009 B1
(45) Date of Patent: Jan. 6, 2004

(54) ADJUSTMENT CLAMP

(75) Inventors: John C. Vanden Hoek, Elk River, MN (US); Jody Rivers, Milaca, MN (US); James Edgard Cox, Corcoran, MN (US); Craig Robert Schlawin, Farmington, MN (US); J. Edward Shapland, Vadnais Heights, MN (US)

(73) Assignee: Acorn Cardiovascular, Inc., St. Paul, MN (US)

( * ) Notice: Subject to any disclaimer, the term of this patent is extended or adjusted under 35 U.S.C. 154(b) by 173 days.

(21) Appl. No.: 09/708,912

(22) Filed: Nov. 8, 2000

(51) Int. Cl.[7] .............................................. A61E 13/00
(52) U.S. Cl. ........................................ 600/37; 606/158
(58) Field of Search ..................... 600/37, 16; 128/898; 606/158, 207, 205, 232, 145; 72/409.1; 607/2; 29/237, 269; 81/300, 234, 370, 363, 9.3, 424.5, 367, 418; 269/756, 93; 30/90.6

(56) References Cited

U.S. PATENT DOCUMENTS

| 3,454,009 | A | | 7/1969 | Hunnicutt |
| 3,783,873 | A | * | 1/1974 | Jacobs ........................ 606/145 |
| 4,161,951 | A | * | 7/1979 | Scanlan ....................... 606/145 |
| 4,407,493 | A | * | 10/1983 | Okolischan .................. 269/93 |
| 4,452,244 | A | | 6/1984 | Chin |
| 4,709,601 | A | * | 12/1987 | Petersen ...................... 81/367 |
| 4,972,583 | A | * | 11/1990 | Pinchon ...................... 30/90.6 |
| 5,012,666 | A | * | 5/1991 | Chen et al. ............... 72/409.01 |
| 5,056,385 | A | * | 10/1991 | Petersen ...................... 81/370 |
| 5,469,765 | A | * | 11/1995 | Franklin ...................... 81/234 |
| 5,593,424 | A | * | 1/1997 | Northrup, III .............. 606/232 |
| 5,644,960 | A | * | 7/1997 | O'Brien ....................... 81/363 |
| 5,855,590 | A | * | 1/1999 | Malecki et al. ............. 606/205 |
| 5,865,072 | A | * | 2/1999 | Jerdee .......................... 81/9.3 |
| 6,076,013 | A | * | 6/2000 | Brennan et al. ................ 607/2 |
| 6,110,100 | A | * | 8/2000 | Talpade ........................ 600/37 |
| 6,128,943 | A | * | 10/2000 | Lemmens ................. 72/409.01 |
| 6,175,998 | B1 | * | 1/2001 | Leo .............................. 29/269 |
| 6,193,648 | B1 | * | 2/2001 | Krueger ....................... 600/37 |
| 6,260,552 | B1 | * | 7/2001 | Mortier et al. .............. 128/898 |
| 6,290,219 | B1 | * | 9/2001 | Barbosa ....................... 269/756 |
| 6,293,906 | B1 | * | 9/2001 | Vanden Hoek et al. ....... 600/37 |
| 6,312,445 | B1 | * | 11/2001 | Forgaty et al. ............. 606/207 |
| 6,314,629 | B1 | * | 11/2001 | Schowalter, Sr. et al. ..... 29/237 |
| 6,332,863 | B1 | * | 12/2001 | Schweich, Jr. et al ........ 600/16 |
| 2001/0049540 | A1 | * | 12/2001 | Santilli ....................... 606/158 |

FOREIGN PATENT DOCUMENTS

DE     36 00 789 A1     7/1987
GB     966277     8/1964

* cited by examiner

Primary Examiner—Teresa Walberg
Assistant Examiner—Leonid M Fastovsky
(74) Attorney, Agent, or Firm—Merchant & Gould P.C.

(57) ABSTRACT

An adjustment clamp suitable for adjusting the tension of a material such as a cardiac support device. The adjustment clamp comprises a pair of interconnected, intersecting arms capable of rotating around a common axis. The arms each comprise a handle, a jaw and a shaft between the handle and jaw. The clamp also includes a latch operably mounted to the handle, wherein the latches of the two arms are capable of engaging each other to secure the clamp at a desired position. In one embodiment, the jaw comprises a flat contact surface. In another embodiment, at least one jaw of one arm comprises a roller assembly. Preferably, the clamp also includes a turning mechanism operably mounted to at least one roller assembly. Methods for using the adjustment claim to increase tension in a material are also described. In a preferred embodiment, the clamp is used to adjust the tension of a cardiac support device.

24 Claims, 7 Drawing Sheets

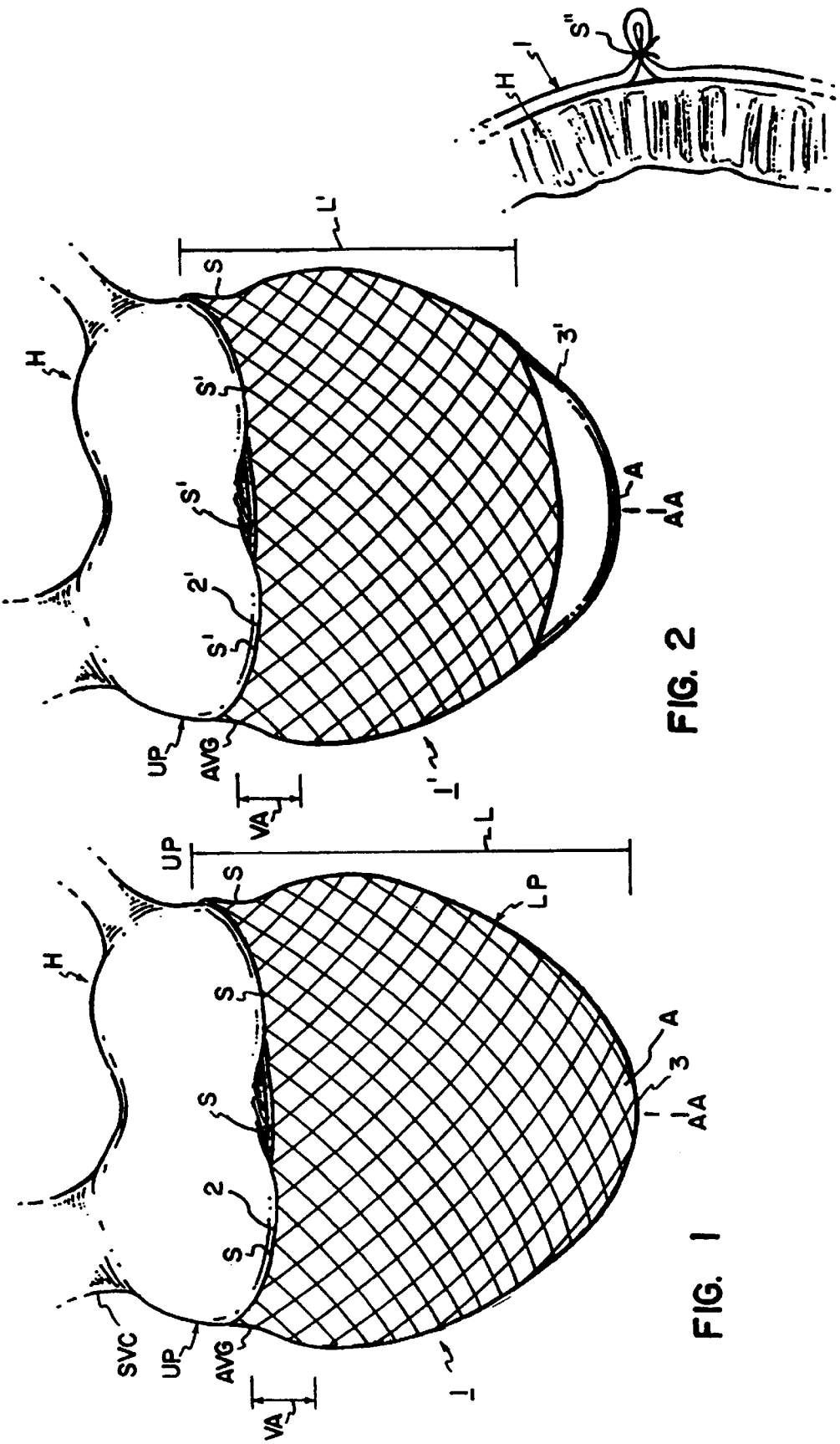

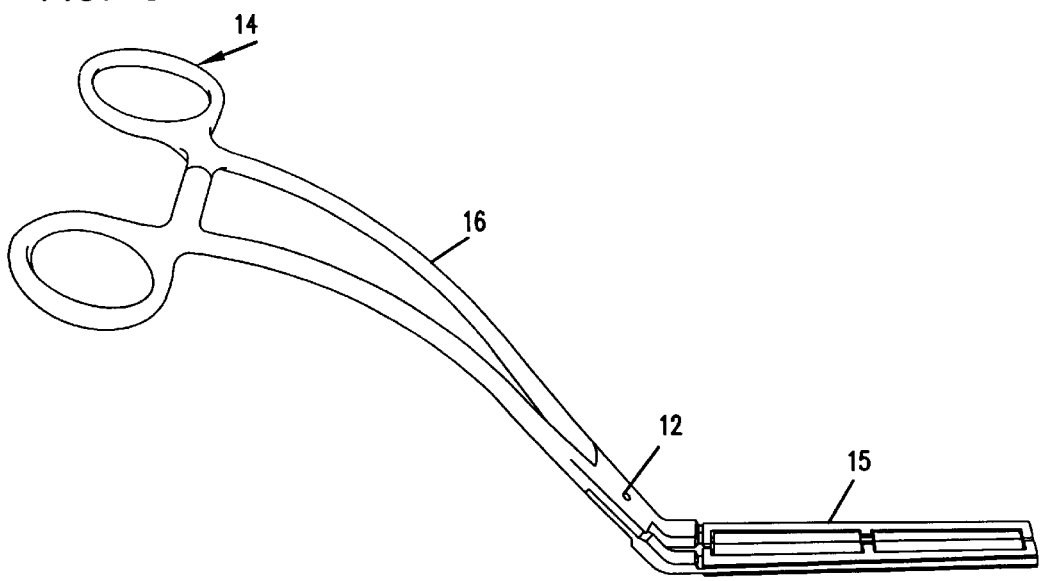
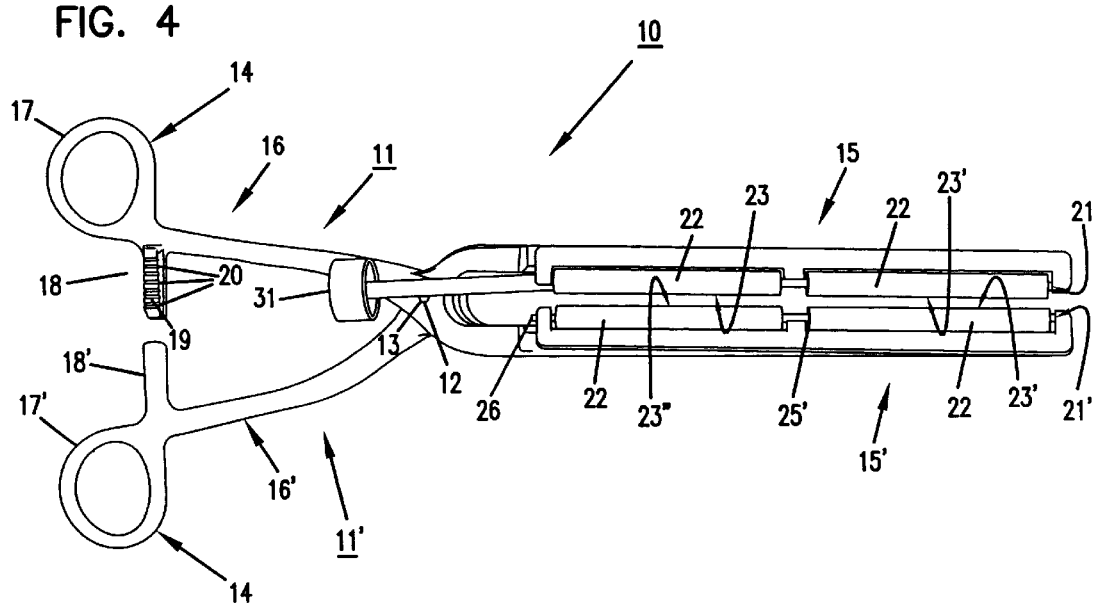

ADJUSTMENT CLAMP

BACKGROUND OF THE INVENTION

1. Field of the Invention

The present invention pertains to a device and method for treating heart disease. More particularly, the present invention is directed to a method and device for treating congestive heart disease and related valvular dysfunction.

2. Description of the Prior Art

Congestive heart disease is a progressive and debilitating illness. The disease is characterized by a progressive enlargement of the heart. As the heart enlarges, the heart is performing an increasing amount of work in order to pump blood each heart beat. In time, the heart becomes so enlarged the heart cannot adequately supply blood. An afflicted patient is fatigued, unable to perform even simple exerting tasks and experiences pain and discomfort. Further, as the heart enlarges, the internal heart valves cannot adequately close. This impairs the function of the valves and further reduces the heart's ability to supply blood.

Causes of congestive heart disease are not fully known. In certain instances, congestive heart disease may result from viral infections. In such cases, the heart may enlarge to such an extent that the adverse consequences of heart enlargement continue after the viral infection has passed and the disease continues its progressively debilitating course.

Commonly assigned U.S. Pat. No. 5,702,343 to Alferness dated Dec. 30, 1997 discloses a jacket of biologically compatible material adapted to surround the heart and to be secured to the heart. The jacket is adjustable such that it may be adjusted to snugly conform to an external geometry of the heart and constrain circumferential expansion of the heart beyond the maximum adjusted volume during diastole while permitting unimpeded contraction of the heart during systole. The present invention pertains to an adjustment clamp for adjusting a cardiac support device such as that disclosed in the '343 patent.

SUMMARY OF THE INVENTION

The present invention provides an adjustment clamp suitable for adjusting the tension of a material such as a cardiac support device. The adjustment clamp comprises a pair of intersecting arms interconnected about a common axis wherein the arms are capable of rotating around the common axis. The arms each comprise a handle, a jaw and a shaft connecting the handle and jaw. The handle preferably comprises a finger loop and a latch attached on the inferior surface of the handle. When the handles are pulled together, the latching surface of each latch causes the two arms to interconnect with each other, thereby locking the clamp at a desired position. The jaws of each arm comprise a clamping surface that is operably engaged when the handles are rotated toward each other. In one embodiment, the jaw comprises at least one roller assembly that comprises at least one roller. According to this embodiment, the clamping surface includes the tangent of the roller. The roller assembly may be rotatably mounted within a frame. Preferably, the clamp also includes a turning mechanism operably mounted to at least one roller assembly.

In use, the handles of the clamp are rotated apart and material (for example, a jacket of a cardiac support device) is positioned in contact with the clamping surface. The handles of the clamp are rotated towards one another such that clamping surface engages the material.

According to the invention, the clamping surfaces are biased together such that the clamping force is less than the desired tension of the fabric. When used in connection with a cardiac support device, it is important that the fabric tension not impair cardiac function. Therefore, the clamping force is preferably less than the left ventricular pressure during diastole.

Once the clamp is biased at a desired clamping force, the material is pulled through the clamp. In the roller clamp embodiment, a turning mechanism is rotated to cause at least one roller to rotate. The frictional contact and clamping force between the rollers urges the material between the rollers, thus increasing tension of the material.

The clamping force of the clamping surface may optionally be varied by the position at which the latch is engaged. The clamp is capable of securing the material until the material reaches a tension wherein the load exerted by the material exceeds the clamping force exerted between the clamping surface (also called the "tension limit"). In the roller clamp embodiment, the rollers may continue to rotate after the tension limit is reached, but material is no longer urged between the rollers. Advantageously, the rollers will slip in areas where the tension of the material has reached the tension limit but will continue to urge material between the rollers in other areas where the tension limit has not yet been reached, until the tension across the material is substantially uniform (e.g., at the tension limit).

BRIEF DESCRIPTION OF THE DRAWINGS

FIG. 1 is a side elevation view of a diseased heart in diastole with a first embodiment of a cardiac support device in place;

FIG. 2 is a side elevation view of a diseased heart in diastole with a second embodiment of a cardiac support device in place;

FIG. 3 is a cross-sectional view of a cardiac support device overlying a myocardium and with the material of the device gathered and sutured for a snug fit;

FIG. 4 is a bottom view of an adjustment clamp according to the invention;

FIG. 5 is a side elevation view of an alternate embodiment of an adjustment clamp according to the invention;

DESCRIPTION OF THE PREFERRED EMBODIMENT

Figure 6:
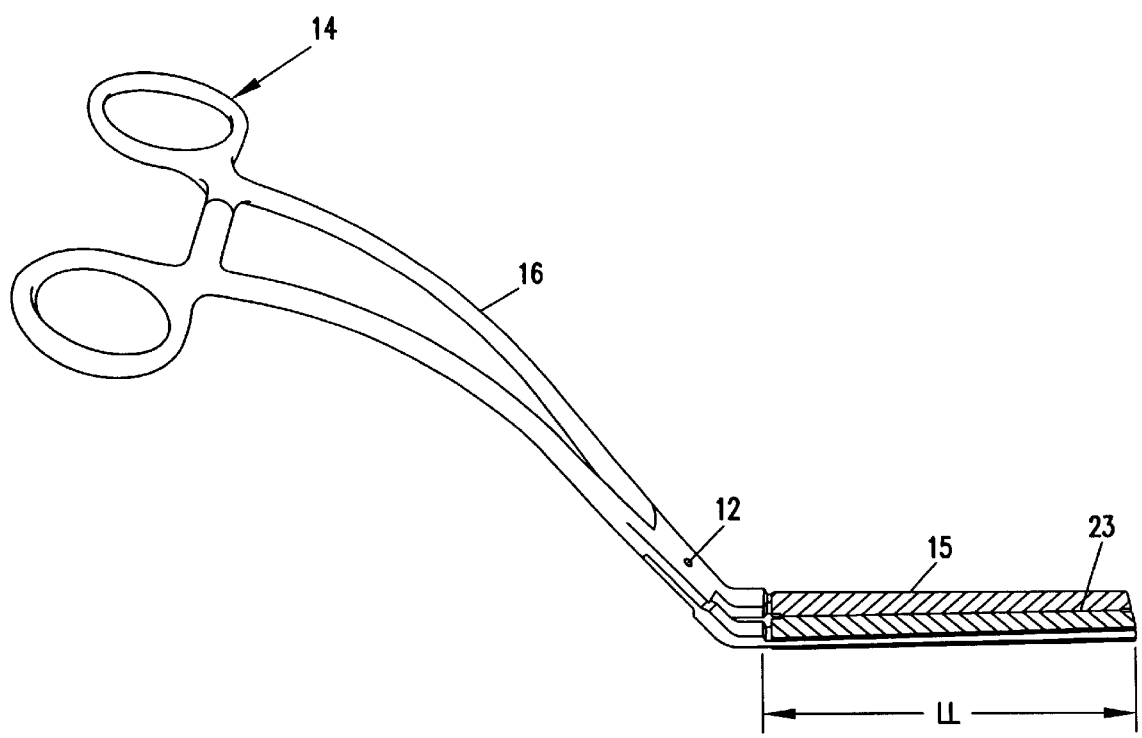
FIG. 6 is a side elevation view of an alternate embodiment of an adjustment clamp according to the invention.

The invention provides an adjustment clamp configured to adjust the tension of a cardiac support device such as that described in commonly assigned U.S. Pat. Nos. 6,085,754 and 5,702,343, the disclosures of which are both incorporated herein by reference. Although the device of the invention is described with reference to a cardiac support device, the clamp may be suitable for use with a variety of other materials, surgical or not. Prior to discussing the adjustment clamp of the invention, a brief discussion of a suitable cardiac support device will be provided.

Cardiac Support Device

In general, a cardiac support device is configured to surround the myocardium of a heart to reduce expansion of the heart wall during diastole by applying constraining surfaces at least at diametrically opposing aspects of the heart such as the cardiac constraint device. Typically, the diametrically opposed surfaces are interconnected, for example, by a continuous material that can substantially encircle the external surface of the heart.

With reference to FIGS. 1 and 2, a cardiac support device is shown as a jacket 1 of flexible, biologically compatible material. The jacket 1 is an enclosed knit material having upper and lower ends 2, 3. In the embodiment of FIG. 1, lower end 3 is closed. In the embodiment of FIG. 2, lower end 3' is open. In both embodiments, upper ends 2, 2' are open.

The jacket 1 is dimensioned with respect to a heart H to be treated. Specifically, the jacket 1 is sized for the heart H to be constrained within the volume defined by the jacket. The jacket 1 can be slipped around the heart H. The jacket 1 has a length L between the upper and lower ends 2, 3 sufficient for the jacket 1 to constrain the lower portion LP of the heart H. The upper end 2 of the jacket 1 extends at least to the valvular annulus VA and further extends to the lower portion LP to constrain at least ventricules of the heart H.

Since enlargement of the lower portion LP of the heart H is generally most troublesome, in a preferred embodiment, the jacket 1 is sized so that the upper end 2 can reside in the A-V groove AVG. Where it is desired to constrain enlargement of the upper portion UP of the heart H, the jacket 1 may be extended to cover the upper portion UP.

Once the jacket 1 is positioned on the heart H, the jacket 1 is secured to the heart. Typically, the jacket 1 is secured to the heart H through sutures. Typically, the jacket 1 is sutured to the heart H at suture locations S circumferentially spaced along the upper end 2 of the jacket 1. While a surgeon may elect to add additional suture locations to prevent shifting of the jacket 1 after placement, the number of such locations S is preferably limited so that the jacket 1 does not restrict contraction of the heart H during systole.

To permit the jacket 1 to be easily placed on the heart H, the volume and shape of the jacket 1 are larger than the lower portion LP during diastole. So sized, the jacket 1 may be easily slipped around the heart H. Once placed, the jacket's volume and shape are adjusted for the jacket 1 to snugly conform to the external geometry of the heart H during diastole. Such sizing is easily accomplished due to the knit construction of the jacket 1. For example, excess material of the jacket 1 can be gathered and sutured S" (FIG. 3) to reduce the volume of the jacket 1 and conform the jacket 1 to the shape of the heart H during diastole. Such shape represents a maximum adjusted volume. The jacket 1 constrains enlargement of the heart H beyond the maximum adjusted volume while preventing restricted contraction of the heart H during systole.

The jacket 1 is adjusted to a snug fit on the heart H during diastole. Care is taken to avoid tightening the jacket 1 too much such that cardiac function is impaired. During diastole, the ventricles of the heart H fill with blood. If the jacket 1 is too tight, the ventricles may not adequately expand and ventricular pressure may rise. During the fitting of the jacket 1, the surgeon can monitor ventricular pressure. For example, a well-known technique for monitoring so-called pulmonary wedge pressure uses a catheter placed in the pulmonary artery. The wedge pressure provides an indication of filling pressure in the left atrium and left ventricle. While minor increases in pressure (e.g., 2–3 mm Hg) can be tolerated, the jacket 1 is snugly fit on the heart H but not so tight as to cause a significant increase in ventricular pressure during diastole.

The jacket 1, freely permits longitudinal and circumferential contraction of the heart H (necessary for heart function). After fitting, the jacket 1 is generally inelastic to prevent further heart enlargement while permitting unrestricted inward movement of the ventricular walls.

If desired, the jacket 1 of the cardiac support device may be soaked in a solvent (such as saline) before placement on the heart.

Adjustment Clamp

The present invention provides an adjustment clamp suitable for adjusting the tension of a material such as a cardiac support device.

Referring now to FIG. 4, the adjustment clamp 10 of the invention comprises a pair of intersecting arms 11, 11' and a common axis 12 interconnecting the intersecting arms 11, 11' wherein the arms 11, 11' are capable of rotating around the common axis 12. Elements in common between the two arms are numbered identically with the addition of an apostrophe to distinguish the second arm. Such elements will not be separately discussed.

The adjustment clamp 10 can be constructed using any suitable material, including metal, such as stainless steel or titanium or plastics such as injection molded plastic, for example, ULTEM® (Monsanto, St. Louis, Mo.). Preferably the arms 11 are constructed from a metal.

The arms 11 of the clamp 10 are pivotally connected at the common axis 12 by a pin 13 or other suitable device placed through the two arms 11. The pin 13 may completely penetrate one or both of the arms 11 or may only partially penetrate one or both arms 11.

The arms 11 each comprise a handle 14, a jaw 15 and a shaft 16 connecting the handle 14 and jaw 15. The handle 14 preferably comprises a finger loop 17 and a latch 18. The finger loop 17 of the handle is generally of a size sufficient to accommodate human fingers. The latch 18 of each handle 14 is attached on the inferior surface of the handle 14 such that the latches 18 of each handle 14 are directly opposed when the two arms 11 of the clamp 10 are pulled together at the handle 14. When the handles 14 are pulled together, the latching surface 19 of each latch 18 engages, thereby engaging the latching teeth 10 and locking the clamp 10 at a desired position. Preferably, the latch 18 comprises multiple teeth 20 on the latching surface 19 such that the handles 14 can be latched at a variety of positions. For example, as the handles 14 of the clamp 10 are brought together, a first set of the teeth 20 are engaged. If additional pressure is applied to urge the handles 14 closer together, a second set of teeth 20 are engaged. If still more pressure is applied, a third set of teeth 20 are engaged. The teeth 20 are released by distorting the arms 11 (typically using the finger loops 17) to temporarily disengage the teeth 20 and allow the clamp 10 to be opened.

The jaw 15 comprises a contact surface 23. In one embodiment, the contact surface 23 comprises an essentially flat surface that is configured to engage the contact surface 23' of the opposing arm 11 (FIG. 6). In a preferred embodiment, the contact surface 23 is smooth. However, the contact surface 23 can be covered with a compliant material (such as expanded silica tubing) to increase frictional contact between the clamping surfaces 61, if desired. Other suitable compliant materials include rubber and urethane. In yet another embodiment, the contact surface 23 can be textured to enhance frictional contact, for example, the surface 61 may be serrated or ribbed. Preferably, the length of the jaw 15 ("LL") is approximately the same (e.g., plus or minus 1 inch) as the length ("L") of the cardiac support device. Generally, the length of the jaw 15 is between about 3 to 4 inches.

Figure 7:
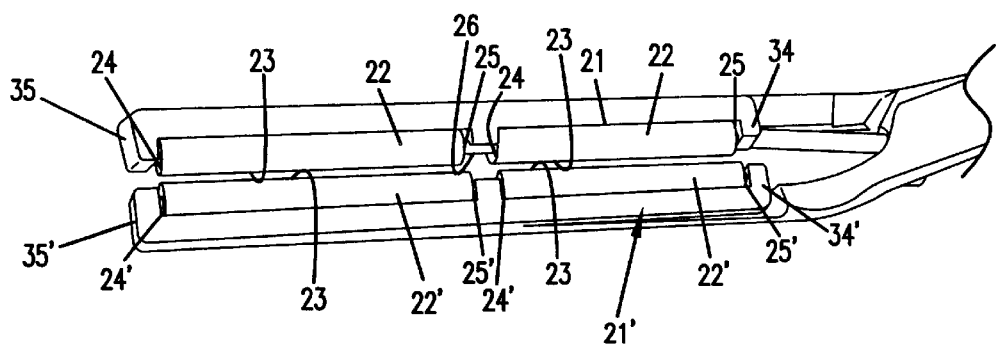
FIG. 7 is a close up top view of a jaw of a clamp according to the invention.

In another embodiment, at least one jaw 15 of the clamp comprises a roller assembly 21 (FIG. 7). In a preferred embodiment, the jaws 15 of each arm 11 comprise roller assemblies 21 that are operably engaged when the handles 14 are rotated toward each other. A roller assembly 21 comprises at least one roller 22 that is generally elongate (e.g., typically between about 3 and 4 inches in length). Generally, the preferred length of the roller 22 and/or roller assembly 21 will be affected by the length of the cardiac support device (10 to 20 cm or 4 to 8 inches) to be tightened. Generally, the roller 22 is cylindrical in shape (having a diameter between about 0.5 and 1.0 inches). The roller diameter is preferably as small as functionally possible, to maintain a low profile.

Figure 8:
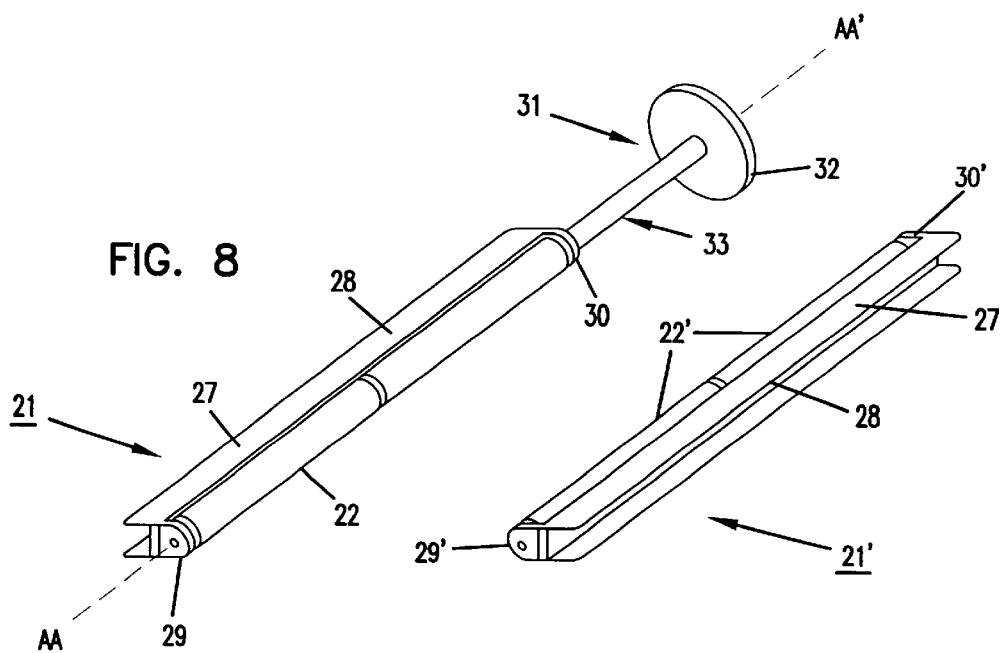
FIG. 8 is an exploded view of the roller assembly of the adjustment clamp.

The roller 22 comprises a contact surface 23 and a first 24 and second 25 face. Generally, an axle 26 is positioned at approximately the center of each face 24, 25 of each roller 22 such that the roller 22 is rotatable about the axle (i.e., the longitudinal axis AA–AA' of the roller 22) (FIG. 8). In one embodiment, the axle 26 extends longitudinally along the axis of the roller 22. In another embodiment, an axle 26 is mounted to each of the first 24 and second 25 faces of the roller 22. The contact surface 23 of each roller is preferably designed to enhance frictional contact. For example, the contact surface 23 of the roller 22 can be compliant. For example, the contact surface 23 of the roller 22 may be covered with a compliant material. In one embodiment, the roller 22 is covered with solvent expanded silica tubing that is placed over the roller and allowed to dry.

Alternately, the roller 22 may be covered with another suitable compliant material, for example, rubber, or urethane. In yet another embodiment, the contact surface 23 of the roller 22 can be textured to enhance frictional contact, for example, the surface 23 may be serrated or ribbed.

In one embodiment, the roller 22 is mounted to the arm 11 of the clamp 10 using the arm 11 as an axle 26. Alternately, the roller assembly 21 may comprise an elongate frame 27. Generally, the frame 27 comprises a longitudinal support 28 and a first 29 and second 30 receiving end. Each receiving end 29, 30 comprises a mechanism, such as an aperture or lip, for receiving the roller 22 axle 26 such that the axle 26 is rotatably mounted within the frame 27. When the handles 14 of the clamp 10 are rotated towards one another and the latch 18 is engaged, the longitudinal axes AA–AA' of the rollers 22 are substantially parallel. The contact surfaces 23 of the rollers 22 may or may not be in frictional contact.

The clamp 10 also includes a turning mechanism 31 operably mounted to at least one roller assembly 21 via a draft shaft 33. The turning mechanism 31 includes a control lever 32 configured to be manually or automatically rotated about an axis to cause the roller 22, to which it is operably connected, to rotate. In one embodiment, the turning mechanism 31 and drive shaft 33 are coaxial with a longitudinal axis AA–AA' of the roller 22. In an alternate embodiment, the drive shaft 33 is not coaxial with the longitudinal axis AA–AA' of the roller 22. For example, the drive shaft 33 may be operably connected to the roller 22 by a universal joint. The control lever 32 may be rotated about the longitudinal axis AA–AA' in either a counterclockwise or clockwise direction. In a preferred embodiment, the clamp 10 includes only one turning mechanism 31 operably mounted to a first roller assembly 21, wherein the first roller assembly 21 functions as a driver and the second (or remaining) roller assembly 21 is passive.

The handle 14, jaw 15 and shaft 16 of each arm 11 may be in substantially the same plane. Alternately, the shaft 16 is non-linear such that the handle 14 and jaw 16 of the arms 11 are essentially parallel, but lying in a different plane (See FIG. 5).

Figure 9:
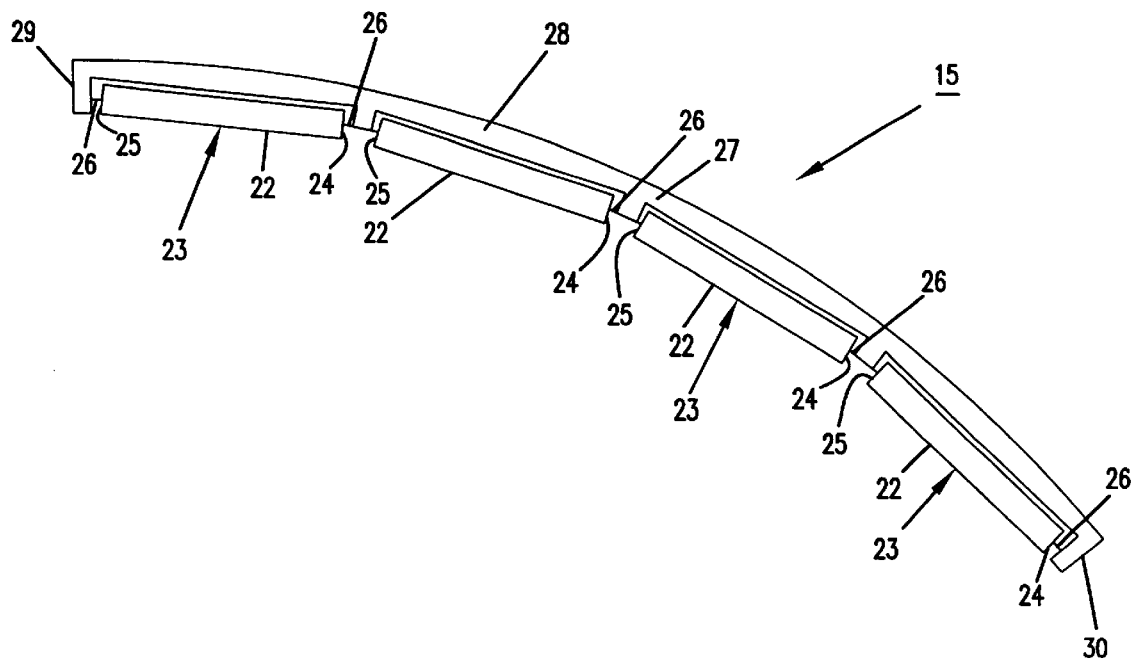
FIG. 9 is a partial side elevation view of an alternate embodiment of an adjustment clamp according to the invention.

In one embodiment, the jaw 15 is substantially linear. In an alternate embodiment, the jaw 15 is non-linear. (See, FIG. 9). If the jaw 15 comprises a roller assembly 21 and is curved, each roller assembly 21 preferably comprises more than one roller 22. In this embodiment, the plurality of rollers 22 are preferably operably connected, for example, with a universal joint or torque cable, such that rotation of a first roller 22 drives the neighboring rollers to rotate in the same direction (e.g., clockwise or counterclockwise).

In use, the handles 14 of the clamp 10 are rotated apart and material (for example, a jacket 1 of a cardiac support device) is positioned between the contact surfaces 23 of the jaws 15. The handles 14 of the clamp 10 are rotated towards one another to engage the latch 18 such that the contact surfaces 23 engage the material. (The force exerted between the contact surfaces 23 is referred to as the clamping force). If the jaws 15 comprise a flat contact surface 23 (FIG. 6), the material is pulled through the jaws 15 of the clamp. In one embodiment, the material is pulled through the jaws 15 manually. The clamp 10 will secure the material until the material reaches a tension wherein the load exerted by the material exceeds the clamping force exerted between the contact surfaces 23 of the jaws 15 (also called the "tension limit").

If the clamp 10 includes at least one roller assembly 21, the control lever 32 is rotated to cause the driver roller 22 to rotate. The frictional contact and clamping force between the rollers 22 urges the material between the rollers 22, thus increasing tension of jacket 1 of the cardiac support device. Once the material reaches a tension wherein the load exerted by the material exceeds the clamping force exerted between the rollers 22 (also called the "tension limit"), the rollers 22 may continue to rotate, but material is no longer urged between the rollers 22. In other words, the rollers 22 "slip". Advantageously, the rollers 22 will "slip" in some areas where the tension of the material has reached the tension limit but will continue to urge material between the rollers 22 in other areas where the tension limit has not yet been reached until the tension across the jacket 1 at the tension limit.

Figure 10:
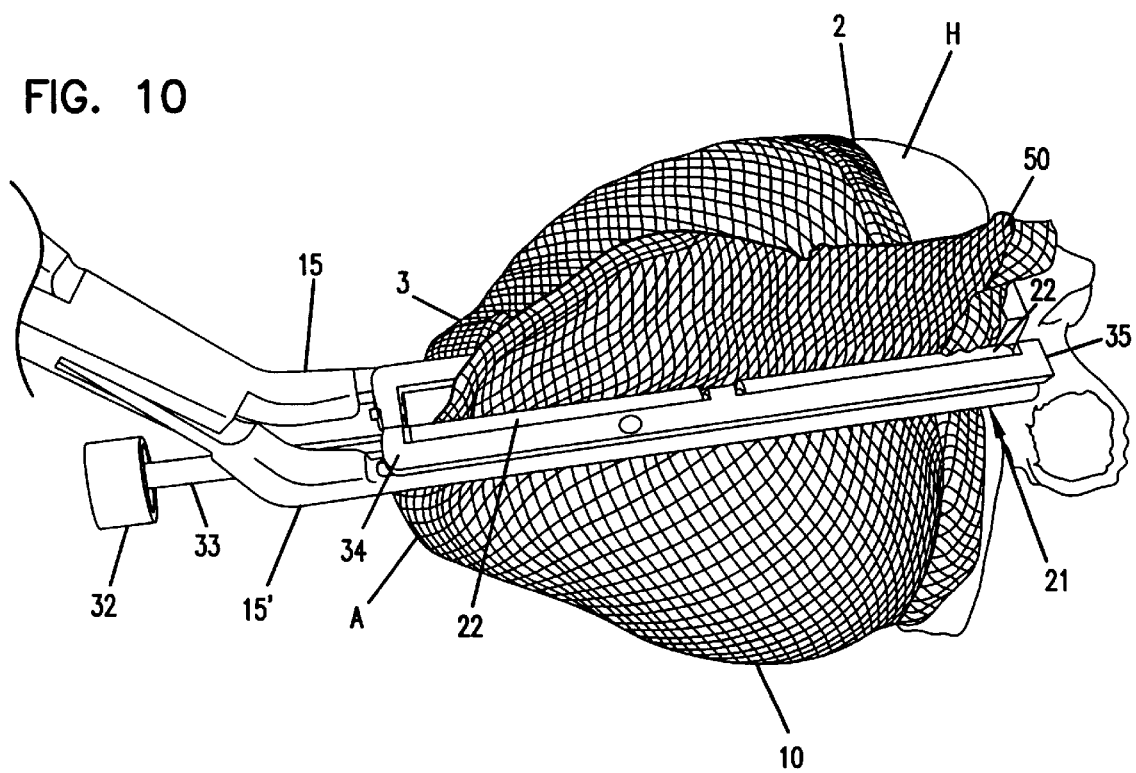
FIG. 10 is a side elevation view of the adjustment clamp in use.

Once the desired tension of the jacket 1 has been obtained, the excess material 50 of the jacket 1 can be cut along the top of the clamp 10 and sutured. (FIG. 10)

Generally, as the handles 14 of the clamp 10 are urged closer together the clamping force exerted between the contact surfaces 23 of the jaws 15 increases, thus increasing the "tension limit" of the material. Accordingly, the handles 14 of the clamp 10 are preferably configured to be latched in a variety of positions by the teeth 20 of the latch 18 such that various "tension limits" can be achieved. The final tension of the material is determined by the tension at which the jaws 15 no longer secure the fabric from the cardiac support device (e.g., the rollers 22 are slipping across the entire contact surface 23).

Preferably the contact surfaces 23 of the jaw 15 are biased together such that the clamping force exerted between the contact surfaces 23 of the jaws 15 is less than the desired tension of the fabric. When used in connection with a cardiac support device, it is important that the fabric tension not impair cardiac function. Preferably the clamping force between the contact surfaces 23 is less than the left ventricular pressure of the heart during diastole.

In use with a cardiac support device, the proximate end 34 of the clamp 10 (i.e., the part of the jaw 15 proximate the common axis) is preferably positioned proximate apex A of the heart. (FIG. 10) Generally, the tension limit at the distal end 35 of the clamp (e.g., proximate the upper end 2 of the jacket 1 when in used) tends to be lower than the tension limit proximate the proximate end 34 of the clamp (e.g., proximate the lower end 3 of the jacket 1 in use). Typically, the tension limit at the distal end 35 of the clamp 10 is between about 0.04 pounds to 0.05 pounds whereas the tension limit at the proximate end 34 of the clamp 10 is between about 0.07 and 0.10 pounds.

Rail Mounted Cardiac Support Device Adjustment Clamp

Figure 11:
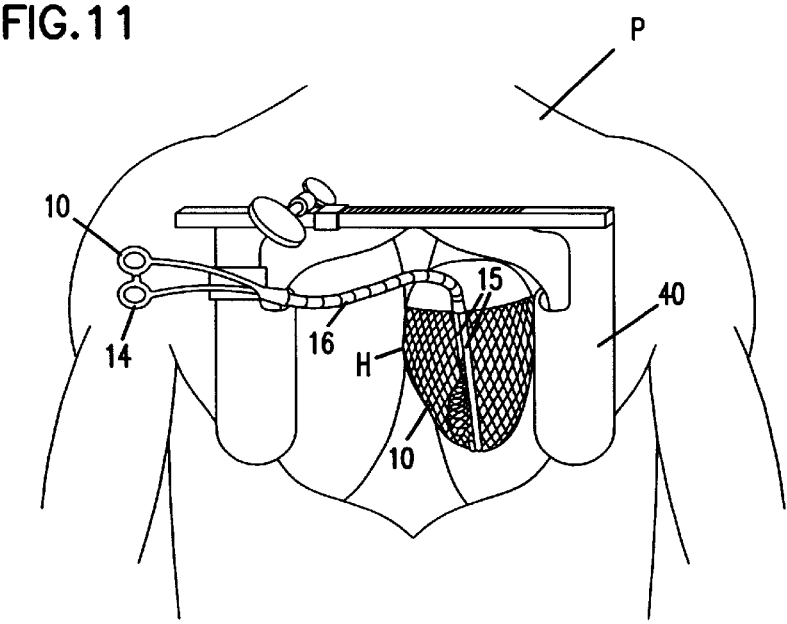
FIG. 11 is an illustration of an alternate embodiment of the adjustment clamp in use.

Optionally, the clamp 10 of the invention, a conventional surgical clamp, such as a DeBakey clamp, available from Scanlan International (Minneapolis, Minn.) can be attached to an apparatus that is maintained stationary relative to the patient P (herein referred to as a "stationary apparatus 40") (FIG. 11). For example, the stationary apparatus 40 can be mounted to the patient's thorax or chest. One example of a stationary apparatus 40 is a rib retractor.

Figure 12:
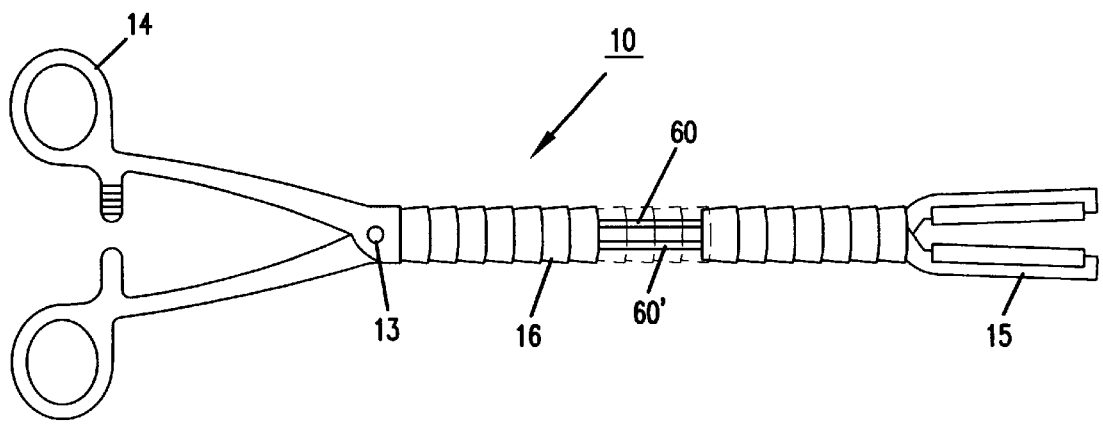
FIG. 12 is a top view of a clamp with a malleable shaft.

In a preferred embodiment, a clamp 10 having a malleable shaft is mounted to the stationary apparatus 40. For example, a clamp 10 with a malleable metal shaft can be used. Alternately, a clamp 10 with a segmented shaft can be used (for example, the V. Mueller segmented surgical clamp commercially available from Allegiance Corporation) in which at least one wire 60 is run through the malleable shaft 16 such that, when the handles 14 are latched together, the wire 60 is drawn taut, thereby bringing the jaws 15 of the clamp 10 together. (FIG. 12)

According to this embodiment, the clamp 10 is mounted to the stationary apparatus 40 in such a manner that operating medical personnel would not have to hold onto the clamp during surgery, thereby providing hands-free operation and increasing the field of vision. (See FIG. 11) Advantageously, when the clamp 10 is mounted to the stationary apparatus 40, the weight of the clamp handles 14 is less likely to inadvertently reposition the cardiac support device I because the clamp 10 is less likely to move relative to the patient P.

EXAMPLES

Example 1

Roller Clamp Study

Proocedure

A cardiac support device (Model No. 77-0109-002 available from Acorn Cardiovascular, Inc., St. Paul, Minn.) was soaked in a saline solution for 0.2 minutes and then placed on a model heart. A Sensotec load cell (part no. 20-0514-001; calibration no. ME-050-0, available from Sensotec (Columbus, Ohio) was calibrated down to 0.001 pounds and placed between the cardiac support device and the cardiac surface at predetermined location on the heart.

Figure 14:
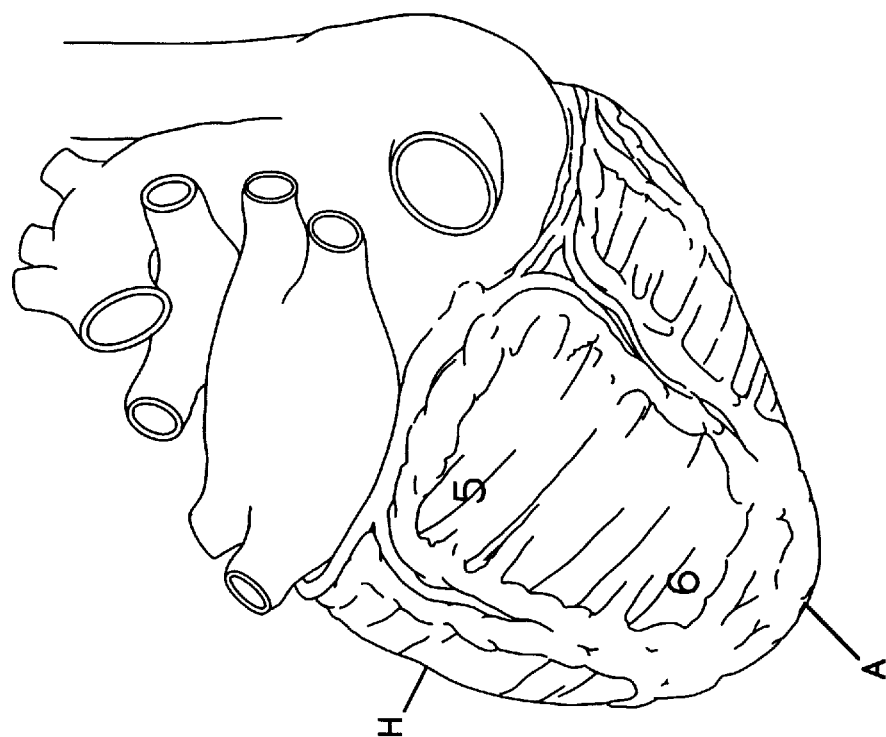
FIGS. 13 and 14 are side elevation views of a heart indicating clamping locations used in the Examples 1 and 2.
Figure 13:
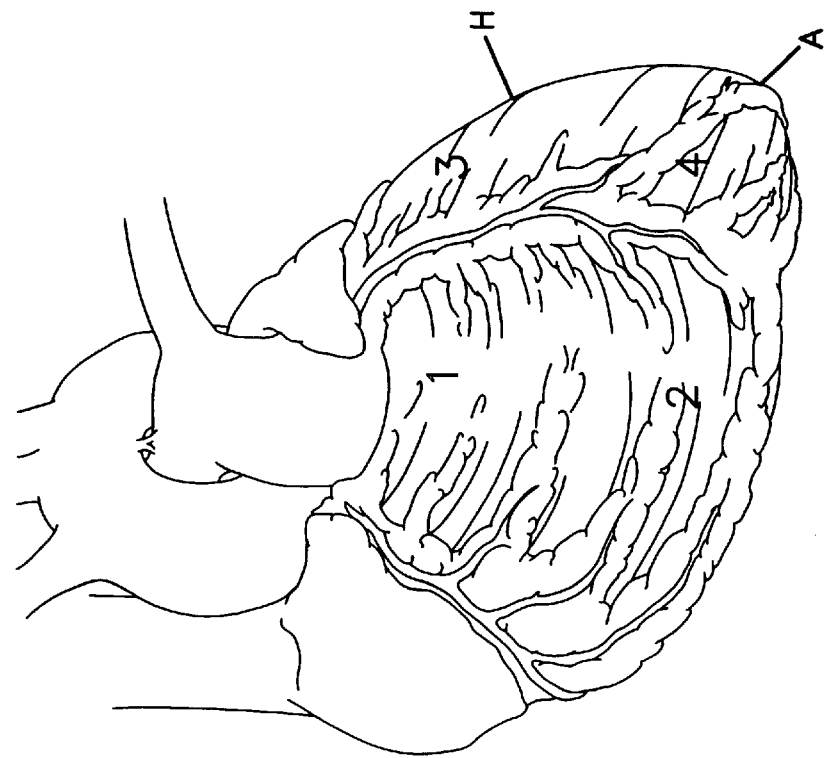

The proximal end of the clamp was positioned at the apex of the heart and the cardiac support device was tightened until the rollers slipped across the entire clamping surface. The load in pounds was then recorded. This procedure was repeated at six locations on the model heart. (See FIGS. 13 and 14) These six locations are considered as one group. The measurements were performed for five groups.

Results:

|  | Group | | | | | | Std |
|---|---|---|---|---|---|---|---|
|  | 1 | 2 | 3 | 4 | 5 | Avg. | Deviation |
| Location 1 | 0.053 | 0.056 | 0.048 | 0.055 | 0.048 | 0.052 | 0.003808 |
| 2 | 0.059 | 0.060 | 0.065 | 0.049 | 0.051 | 0.057 | 0.006648 |
| 3 | 0.048 | 0.055 | 0.049 | 0.060 | 0.045 | 0.051 | 0.006025 |
| 4 | 0.012 | 0.085 | 0.100 | 0.070 | 0.110 | 0.097 | 0.019875 |
| 5 | 0.030 | 0.053 | 0.049 | 0.044 | 0.058 | 0.047 | 0.010710 |
| 6 | 0.090 | 0.110 | 0.070 | 0.069 | 0.085 | 0.085 | 0.016814 |
| Avg | 0.067 | 0.070 | 0.064 | 0.056 | 0.066 | | |
| Std Deviation | 0.032641 | 0.022956 | 0.020187 | 0.010534 | 0.025888 | | |
| | | | | | All 30 Readings | Avg. | 0.0648 |
| | | | | | | Std. Dev. | 0.022276 |

Generally, the force applied between the model heart and the cardiac support at the tension limit fell between 0.03 and 0.12 pounds. The averages of locations 1, 3 and 5 (which are all near the hem area of the cardiac support device) are 0.052, 0.051 and 0.047 pounds, respectively, and are very close in value, although they are lower than the averages of locations 2, 4 and 6 (0.075, 0.097 and 0.085, respectively) which are also close to each other (near the apex of the cardiac support device).

Conclusion

The roller clamp showed repeatability in force applied each time it was used. Additionally, the cardiac support device was tightened uniformly around the heart. Furthermore, when the fabric of the device starts slipping at the tightest point, it continues to take up excess fabric along the rest of the device.

Example 2

Fresh Pig Heart

The same experiment described above in Example 1 was performed on a fresh pig heart (i.e., a heart obtained from a pig on the day it was sacrificed).

| | Results: | | | | | | |
|---|---|---|---|---|---|---|---|
| | Group | | | | | Avg. | Std Deviation |
| | 1 | 2 | 3 | 4 | 5 | | |
| Location 1 | 0.025 | 0.031 | 0.028 | 0.028 | 0.027 | 0.0278 | 0.002168 |
| 2 | 0.030 | 0.025 | 0.020 | 0.028 | 0.029 | 0.0264 | 0.004037 |
| 3 | 0.029 | 0.017 | 0.017 | 0.029 | 0.023 | 0.0230 | 0.006000 |
| 4 | 0.032 | 0.032 | 0.032 | 0.027 | 0.024 | 0.0294 | 0.003715 |
| 5 | 0.025 | 0.028 | 0.023 | 0.020 | 0.022 | 0.0236 | 0.003050 |
| 6 | 0.029 | 0.026 | 0.031 | 0.029 | 0.032 | 0.0294 | 0.002302 |
| Avg | 0.028333 | 0.026500 | 0.025167 | 0.026833 | 0.026167 | | |
| Std Deviation | 0.002805 | 0.005394 | 0.006113 | 0.003430 | 0.003869 | | |
| | | | | All 30 Readings | | Avg. Std. Dev. | |

Conclusion

As with Example 1, the roller clamp showed repeatability in force applied each time it was used and was tightened uniformly around the heart. Again, the device continued to take up excess fabric along the rest of the device when the fabric of the device began slipping at the tightest point.

What is claimed is:

1. A clamp for tensioning a cardiac support device, said cardiac support device configured for treating cardiac disease of a heart having a left diastolic ventricular pressure, said clamp comprising:
   a first and a second intersecting arm wherein each arm comprises:
      a handle comprising a latching mechanism;
      a jaw comprising a contact surface; and
      a shaft connecting said handle and said jaw,
   wherein said latching mechanism is configured to bias said contact surfaces of said jaws together at a clamping force that is less than the left diastolic ventricular pressure of said heart and wherein at least one jaw of said clamp comprises a roller assembly.

2. A clamp comprising:
   a first and a second intersecting arm wherein each arm comprises:
      a handle;
      a jaw, wherein said jaw has a longitudinal axis, and at least one jaw of said clamp comprises a roller assembly comprising at least one roller, wherein said roller is rotatable around an axis that is aligned with said longitudinal axis of said jaw; and
      a shaft connecting said handle and said jaw; and
   a turning mechanism operably mounted to at least one roller assembly.

3. A device according to claim 2, wherein said handle further comprises a finger loop.

4. A device according to claim 2, wherein each handle further comprises a latch mounted to an inferior surface of said handle wherein said latch of said first arm directly opposes said latch of said second arm when said arms of said clamp are rotated towards each other.

5. A device according to claim 4, wherein said latch comprises a latching surface with a plurality of latching teeth.

6. A device according to claim 2, wherein said roller assembly comprises at least one roller.

7. A device according to claim 6, wherein said roller is operably mounted to a frame.

8. A device according to claim 6, wherein said roller comprises an axle, said axle comprising said arm of said clamp.

9. A device according to claim 2, wherein said roller assembly comprises a plurality of rollers.

10. A device according to claim 6, wherein said roller comprises a contact surface.

11. A device according to claim 10, wherein said contact surface is compliant.

12. A device according to claim 10, wherein said contact surface comprises silica tubing.

13. A device according to claim 10, wherein said contact surface is textured.

14. A device according to claim 13, wherein said contact surface is serrated or ribbed.

15. A device according to claim 2, wherein said turning mechanism comprises a control lever capable of being manually or automatically rotated.

16. A device according to claim 2, wherein said turning mechanism is operably connected to one roller assembly.

17. A device according to claim 2, wherein said roller assembly is substantially linear.

18. A device according to claim 2, wherein said roller assembly is non-linear.

19. A device according to claim 18, wherein said roller assembly comprises a plurality of operably connected rollers.

20. A method for increasing tension in a material, comprising:
   providing a clamp, said clamp comprising:
      a first and a second arm, said arms intersecting at a common axis, wherein each arm comprises:
         a handle;
         a jaw, wherein said jaw comprises a contact surface; and
         a shaft connecting said handle and said jaw;
   rotating said handles in a plane around said common axis to open said jaw;
   positioning said material between said contact surfaces of said jaws;
   frictionally engaging said material with said contact surfaces of said jaw; and
   urging said material through said jaws of said clamp in a direction substantially perpendicular to said plane of rotation, and wherein said jaw of at least one arm comprises a roller assembly and a turning mechanism and said turning mechanism is employed to rotate at least one roller, thereby urging said material between said rollers.

21. A method according to claim 1, further comprising a step of cutting said material along said clamp and suturing said material once a desired tension of said material has been obtained.

22. A method according to claim 1, wherein said material comprises a cardiac support device.

23. A method according to claim 22, wherein said cardiac support device is positioned on a heart having a longitudinal axis from an apex to a base and ventricular lower extremities adjacent said apex, said cardiac support device comprising:

a jacket of flexible material of knit construction defining a volume between an open upper end and a lower end, said jacket dimensioned for said apex of said heart to be inserted into said volume through said open upper end and for said jacket to be slipped over said heart, said jacket further dimensioned for said jacket to have a longitudinal dimension between said upper and lower ends sufficient for said jacket to constrain said ventricular lower extremities.

24. A method according to claim 23, further comprising a step of positioning a first end of said jaws, proximate said common axis, proximate said apex of said heart.

\* \* \* \* \*

UNITED STATES PATENT AND TRADEMARK OFFICE
CERTIFICATE OF CORRECTION

PATENT NO. : 6,673,009 B1
DATED : January 6, 2004
INVENTOR(S) : Vanden Hoek et al.

It is certified that error appears in the above-identified patent and that said Letters Patent is hereby corrected as shown below:

Title page,
Item [75], Inventors, "James Edgard Cox," should read -- James Edgar Cox, --
Item [56], References Cited, U.S. PATENT DOCUMENTS, insert the following:

| | | |
|---|---|---|
| --3,983,863 | 10/1976 | Janke et al. |
| 4,048,990 | 9/1977 | Goetz |
| 4,428,375 | 1/1984 | Ellman |
| 4,630,597 | 12/1986 | Kantrowitz et al. |
| 4,690,134 | 9/1987 | Snyders |
| 4,821,723 | 4/1989 | Baker, Jr. et al. |
| 4,878,890 | 11/1989 | Bilweis |
| 4,936,857 | 6/1990 | Kulik |
| 4,957,477 | 9/1990 | Lundbäck |
| 4,973,300 | 11/1990 | Wright |
| 4,976,730 | 12/1990 | Kwan-Gett |
| 5,057,117 | 10/1991 | Atweh |
| 5,087,243 | 2/1992 | Avitall |
| 5,131,905 | 7/1992 | Grooters |
| 5,150,706 | 9/1992 | Cox et al. |
| 5,186,711 | 2/1993 | Epstein |
| 5,192,314 | 3/1993 | Daskalakis |
| 5,256,132 | 10/1993 | Snyders |
| 5,290,217 | 3/1994 | Campos |
| 5,356,432 | 10/1994 | Rutkow et al. |
| 5,383,840 | 1/1995 | Heilman et al. |
| 5,385,156 | 1/1995 | Oliva |
| 5,429,584 | 7/1995 | Chiu |
| 5,507,779 | 4/1996 | Altman |
| 5,524,633 | 6/1996 | Heaven et al. |
| 5,603,337 | 2/1997 | Jarvik |
| 5,647,380 | 7/1997 | Campbell et al. |
| 5,702,343 | 12/1997 | Alferness |
| 5,713,954 | 2/1998 | Rosenberg et al. |
| 5,800,528 | 9/1998 | Lederman et al. |
| 5,961,440 | 10/1999 | Schweich, Jr. et al. |
| 5,990,378 | 11/1999 | Ellis |
| 6,045,497 | 4/2000 | Schweich, Jr. et al. |
| 6,050,936 | 4/2000 | Schweich, Jr. et al. |
| 6,059,715 | 5/2000 | Schweich, Jr. et al.-- |

UNITED STATES PATENT AND TRADEMARK OFFICE
CERTIFICATE OF CORRECTION

PATENT NO. : 6,673,009 B1
DATED : January 6, 2004
INVENTOR(S) : Vanden Hoek et al.

It is certified that error appears in the above-identified patent and that said Letters Patent is hereby corrected as shown below:

Title page (cont;d),
FOREIGN PATENT DOCUMENTS, insert the following:

| -- DE | 295 17 393 U1 | 3//1996 |
| EP | 0 280 564 A2 | 8/1988 |
| JP | 60-203250 | 10/1985 |
| JP | 01-145066 | 6/1989 |
| WO | WO 98/29041 | 7/1998 |
| WO | WO 98/58598 | 12/1998 |
| WO | WO 99/44534 | 9/1999 |
| WO | WO 00/06026 | 2/2000 |
| WO | WO 00/06027 | 2/2000 |
| WO | WO 00/06028 | 2/2000 |
| WO | WO 00/16700 | 3/2000 |
| SU | 1009457 A | 4/1983-- |

OTHER PUBLICATIONS, insert the following:

--"Supplement to Circulation", *Abstracts from the 68th Scientific Sessions*, Vol. 92, No. 8, 2 pages (October 15, 1995).

Capomolla, S. et al., "Dobutamine and nitroprusside infusion in patients with severe congestive heart failure: Hemodynamic improvement by discordant effects on mitral regurgitation, left atrial function, and ventricular function", *American Heart Journal*, Vol. 134, pp. 1089-1098 (December 1997).

Capouya, E. et al., "Girdling Effect of Nonstimulated Cardiomyoplasty on Left Ventricular Function", *Ann Thorac. Surg.*, Vol. 56, pp. 867-871 (1993).

Cohn, J., "The Management of Chronic Heart Failure", *The New England Journal of Medicine*, Vol. 335, No. 7, pp. 490-498 (August 15, 1996).

Coletta, C. et al., "Prognostic value of left ventricular volume response during dobutamine stress echocardiography", *European Heart Journal*, Vol. 18, pp. 1599-1605 (October 1997).

Guasp, F., "Una prótesis contentiva para el tratamiento de la miocardiopatía dilatada", *Revista Española de Cardiología*, Vol 51, No. 7, pp. 521-528 (July 1998).

Kass, D. et al., "Reverse Remodeling From Cardiomyoplasty in Human Heart Failure External Constraint Versus Active Assist", *Circulation*, Vol. 91, No. 9, pp. 2314-2318 (May 1, 1995).

UNITED STATES PATENT AND TRADEMARK OFFICE
CERTIFICATE OF CORRECTION

PATENT NO.    : 6,673,009 B1
DATED         : January 6, 2004
INVENTOR(S)   : Vanden Hoek et al.

It is certified that error appears in the above-identified patent and that said Letters Patent is hereby corrected as shown below:

OTHER PUBLICATIONS (cont'd),

Levin, H. et al., "Reversal of Chronic Ventricular Dilation in Patients With End-Stage Cardiomyopathy by Prolonged Mechanical Unloading", *Circulation*, Vol. 91, No. 11, pp. 2717-2720 (June 1, 1995).

Oh, J. et al., "The Effects Of Prosthetic Cardiac Binding and Adynamic Cardiomyoplasty In A Model Of Dilated Cardiomyopathy", *The Journal of Thoracic and Cardiovascular Surgery*, Vol. 116, No. 1, pp. 148-153 (July 1998)

Paling, D., "Warp Knitting Technology", *Columbine Press*, pg. 111 (1965).

Vaynblat, M. et al., "Cardiac Binding in Experimental Heart Failure", *Ann. Thorac. Surg.*, Vol. 64, 11 pages (1997).--

Column 8,
Line 10, "Proocedure" should read -- Procedure --

Column 11,
Lines 5 and 9, "claim 1," should read -- claim 20, --

Signed and Sealed this

Eighth Day of June, 2004

JON W. DUDAS
*Acting Director of the United States Patent and Trademark Office*